United States Patent
Jin et al.

(10) Patent No.: US 11,879,160 B2
(45) Date of Patent: Jan. 23, 2024

(54) **MOLECULAR MARKER FOR IDENTIFYING TRAIT OF EFFICIENCY OF DUCK FEED UTILIZATION BASED ON NEUROPEPTIDE GENE *NPY*, METHOD AND USE THEREOF**

(71) Applicant: Anhui Agricultural University, Hefei (CN)

(72) Inventors: Sihua Jin, Hefei (CN); Zhaoyu Geng, Hefei (CN); Hongfeng Jiang, Hefei (CN); Fei Shui, Hefei (CN); Jingjing Xia, Hefei (CN); Yuqing Jia, Hefei (CN); Chengcheng Cao, Hefei (CN); Yuanfei Ding, Hefei (CN); Taikang Zhang, Hefei (CN); Fumin Jia, Hefei (CN)

(73) Assignee: Anhui Agricultural University, Hefei (CN)

( * ) Notice: Subject to any disclaimer, the term of this patent is extended or adjusted under 35 U.S.C. 154(b) by 0 days.

(21) Appl. No.: 18/111,150

(22) Filed: Feb. 17, 2023

(65) Prior Publication Data

US 2023/0357867 A1 Nov. 9, 2023

(30) Foreign Application Priority Data

May 9, 2022 (CN) .......................... 202210499498.5

(51) Int. Cl.
*C12Q 1/6888* (2018.01)
(52) U.S. Cl.
CPC ..... *C12Q 1/6888* (2013.01); *C12Q 2600/124* (2013.01); *C12Q 2600/156* (2013.01)
(58) Field of Classification Search
None
See application file for complete search history.

(56) References Cited

FOREIGN PATENT DOCUMENTS

CN 111676295 A 9/2020

OTHER PUBLICATIONS

Tatemoto et al., "Neuropeptide Y-a Novel Brain Peptide with Structural Similarities to Peptide YY and Pancreatic Polypeptide", Nautre, vol. 296, pp. 659-660, Apr. 1982.
Clark et al., "Neuropeptide Y and Human Pancreatic Stimulate Feeding Behavior in Rats", Endocrinology, vol. 115, No. 1, pp. 427-429, Feb. 1984.
Shin, et al., "Elevated Pentraxin 3 in Obese Adipose Tissue Promotes Adipogenic Differentiation by Activating Neuropeptide Y Signaling", Frontiers in Immunology, vol. 9, pp. 1-12, Jul. 2018.
Zhang et al., "Association Analysis Between Variants in Bovine NPY Gene and Growth Traits in Nanyang Cattle (*Bos tarus*)", General and Comparative Endocrinology, vol. 170, pp. 189-192, 2011.
Perkins et al., "Residual Feed Intake Studies in Angus-Sired Cattle Reveal a Potential Role for Hypothalamic Gene Expression in Regulating Feed Efficiency", J. Anim. Sci, pp. 549-560, 2014.

*Primary Examiner* — Sarae L Bausch
(74) *Attorney, Agent, or Firm* — Hoffmann & Baron, LLP

(57) ABSTRACT

The present disclosure provides a molecular marker for identifying traits of efficiency of duck feed utilization based on a neuropeptide gene NPY, a method and use thereof. The NPY gene has a nucleotide sequence shown in SEQ ID NO: 1, the molecular marker is T or C, and the molecular marker is located at position 577 of the nucleotide sequence. In the present disclosure, mutation of the NPY gene is detected using a polymerase chain reaction-single strand conformation polymorphism (PCR-SSCP) method, the traits of efficiency of duck feed utilization are selected based on genotypes, and a breeding method for early selection of efficiency of poultry feed utilization is established. The method is simple, rapid, and low-cost, does not need special instrument, and satisfies experimental needs.

1 Claim, 2 Drawing Sheets
Specification includes a Sequence Listing.

SEQUENCE LISTING

```
Sequence total quantity: 7
SEQ ID NO: 1         moltype = DNA  length = 1200
FEATURE              Location/Qualifiers
source               1..1200
                     mol_type = other DNA
                     note = NPY gene of duck
                     organism = synthetic construct
SEQUENCE: 1
gccggggcta ccgaggcgtg atcgcccgag gcccctcctg cctgccgggg aagacttaaa 60
acagcccggc gaggcgcgga gccccgcact cgggagcccc gacccacggg cacaagcgcc 120
```

-continued

```
tcgcctcgcc cggagccgct ccctccgctg cagccgccgc cgtgagtacc gcgacggggg  180
ggacatgggc atggcgatgg gacacgggat gtgggacatc atggggacgg ggatggggtc  240
gcggggctcg gcgccgaggg ggcgtccgcg ctgctccgcc gtcggggcgg gcgctgacgg  300
cggctctctc cccccggcgt gcagatgcag ggcaccatga ggctgtgggt gtcggtgctg  360
actttcgccc tgtcgctgct cgtctgcctg gggacgctgg cagaagcgta cccctccaaa  420
ccggacagcc ccggcgagga tgcccccgca gaggacatgg ccagatacta ctcggcgctg  480
aggcactaca tcaacctcat caccaggcag aggtaggtgc cggggccctt ctcctcagcg  540
aggtggaagg gagggatgtg gggtgtcccc tcggagccgg gggtcttgcc ctgcttcctt  600
cggggtgagg gggaaccacc ggcaggaaag atgcaggggt catgtaccct ctggagagtg  660
tgagccctgg gactggaggt ggatttccac catccaagtt ggcaaaaagg gcagggtgta  720
catgtctgta ggatagcgtg cgtggggaga gccccccgaa gctgagggaa aatgaaactc  780
acccctggga gtgcaaagta gggcaggagg agcaatttca cgcttctgtt gctgccgctg  840
tctctagtga ggatttagtt gggaaaaaag ttcccctctg tgcttgcaga ggagttgtag  900
tagtttggac gctttatagt ttgtcagcta cttaatacag cagcgagtgc caaaaagccc  960
gtttgtccta acaaaaactc tcaagagcac aaacaagaac ccgtgcccaa gctgaaagag  1020
gagtgagtgt gacccaaagc tgccttgctc tgagctggtt ttctgaggat ggctgcgctg  1080
cttacagtgg cagtggaggt tcagcctgga aaaagtgaaa cttatactat aaaattattt  1140
tatttgggag tgtctgtcca gttttgactg attaatagaa acatccccta aggtccctga  1200

SEQ ID NO: 2            moltype = DNA  length = 23
FEATURE                 Location/Qualifiers
source                  1..23
                        mol_type = other DNA
                        note = Forward primer
                        organism = synthetic construct
SEQUENCE: 2
ggacatggcc agatactact cgg                                           23

SEQ ID NO: 3            moltype = DNA  length = 23
FEATURE                 Location/Qualifiers
source                  1..23
                        mol_type = other DNA
                        note = Reverse primer
                        organism = synthetic construct
SEQUENCE: 3
gggtacatga cccctgcatc ttt                                           23

SEQ ID NO: 4            moltype = DNA  length = 197
FEATURE                 Location/Qualifiers
source                  1..197
                        mol_type = other DNA
                        note = Amplified fragment
                        organism = synthetic construct
SEQUENCE: 4
ggacatggcc agatactact cggcgctgag gcactacatc aacctcatca ccaggcagag  60
gtaggtgccg gggcccttct cctcagcgag gtggaaggga gggatgtggg gtgtcccctc  120
ggagccgggg gtcttgccct gcttccttcg gggtgagggg gaaccaccgg caggaaagat  180
gcaggggtca tgtaccc                                                  197

SEQ ID NO: 5            moltype = DNA  length = 15
FEATURE                 Location/Qualifiers
source                  1..15
                        mol_type = other DNA
                        note = Fragment of NYP gene in D type
                        organism = synthetic construct
SEQUENCE: 5
gggagggacg tgggg                                                    15

SEQ ID NO: 6            moltype = DNA  length = 15
FEATURE                 Location/Qualifiers
source                  1..15
                        mol_type = other DNA
                        note = Fragment of NYP gene in E type
                        organism = synthetic construct
SEQUENCE: 6
gggagggacg tgggg                                                    15

SEQ ID NO: 7            moltype = DNA  length = 15
FEATURE                 Location/Qualifiers
source                  1..15
                        mol_type = other DNA
                        note = Fragment of NYP gene in F type
                        organism = synthetic construct
SEQUENCE: 7
gggagggatg tgggg                                                    15
```

MOLECULAR MARKER FOR IDENTIFYING TRAIT OF EFFICIENCY OF DUCK FEED UTILIZATION BASED ON NEUROPEPTIDE GENE NPY, METHOD AND USE THEREOF

CROSS REFERENCE TO RELATED APPLICATION

This patent application claims the benefit and priority of Chinese Patent Application No. 202210499498.5, filed with the China National Intellectual Property Administration on May 9, 2022, the disclosure of which is incorporated by reference herein in its entirety as part of the present application.

REFERENCE TO SEQUENCE LISTING

A computer readable XML file entitled "GWP20221101022_seqlist.xml" that was created on Aug. 4, 2023, with a file size of about 9,862 bytes, contains the sequence listing for this application, has been filed with this application, and is hereby incorporated by reference in its entirety.

TECHNICAL FIELD

The present disclosure relates to the technical field of molecular markers, in particular to a molecular marker for identifying traits of efficiency of duck feed utilization based on a neuropeptide gene NPY, a method and use thereof.

BACKGROUND

Duck meat is an important source of high-quality protein for Chinese consumers. Duck meat has a unique flavor and is rich in unsaturated fatty acids that are beneficial to human health. It accounts for about 25% of poultry consumption and is favored by consumers. Meat ducks mainly include white feather duck, Shelduck, and Muscovy duck, among which the slaughtering rate of white feather ducks accounts for 80%-90% of the total slaughtering rate of meat ducks. At present, the main breeds of white feather ducks include Cherry Valley duck and Z-type Peking duck. White feather duck Q1 line is a newly bred line, which was bred from six successive generations using parental Maple Leaf duck breeders as breeding materials, but there is a lack of research on the growth and development thereof. The SNP loci of Q1 line ducks were screened by using the NPY gene as a candidate gene affecting slaughter traits, and their effects on slaughter traits were analyzed to provide reference for the continuous breeding, molecular marker-assisted selection, and feeding management of white feather duck Q1 line.

The NPY gene was found in pig brain tissue by Tatemoto et al. in 1982 when they were studying peptide amides. The gene is mainly found in the nerve tissue of animals and has a role in stimulating animal feeding activities and participating in energy metabolism in the body. Thus, it is named neuropeptide (Kazuhiko Tatemoto, Mats Carlquist, and Viktor Mutt. Neuropeptide Y—a novel brain peptide with structural similarities to peptide YY and pancreatic polypeptide[J]. Nature, 1982, 296(5858):659-660.). Clark et al. studied the effect of NPY on feed intake (FI) in adult female rats, and found that NPY had an effect on the feed intake of rats, which stimulated the feeding of satiated rats, and further found that their food intake (FI) was 3 times that of the insulin injection group compared with the rats in the insulin injection group. It could be seen that NPY was a polypeptide that strongly stimulates food intake. Also, the study found that NPY mediated the expression of a plurality of genes, which lad to obesity in the body. For example, NPY not only mediated the expression of the inflammatory factor Pentraxin3, but also promoted the production of reactive oxygen species (ROX), which is one of the known triggering factors of adipogenesis, leading to lipid accumulation in mouse preadipocytes, 3T3-L1 cells (Clark J T, Kalra P S, Crowley W R, et al. Neuropeptide Y and human pancreatic polypeptide stimulate feeding behavior in rats[J]. Endocrinology, 1984, 115(1):427-9; Shin M K, Choi B, Kim E Y, et al. Elevated Pentraxin 3 in Obese Adipose Tissue Promotes Adipogenic Differentiation by Activating Neuropeptide Y Signaling[J]. Front Immunol, 2018, 9: 1790.). In 2011, Zhang et al. studied the NPY gene of Chinese indigenous cattle breeds and found that the gene had an A/C mutation at position 32463 and a C/G mutation at position 32302, and that these mutations were associated with body length and chest girth in Nanyang cattle (a Chinese indigenous cattle breed) aged 6, 12 and 18 months (P<0.05) (Zhang L, Zhang A-L, Zhang L-Z, et al. Association analysis between variants in bovine NPY gene and growth traits in Nanyang cattle (*Bos tarus*)[J]. Gen Comp Endocrinol, 2011, 170(1):189-192.). Perkins et al found that the expression of neuropeptide (NPY) was different between high and low residual feed intake (RFI) Angus-sired steers, and its expression decreased by 64% in the low RFI group (Perkins S D, Key C N, Garrett C F, et al. Residual feed intake studies in Angus-sired cattle reveal a potential role for hypothalamic gene expression in regulating feed efficiency[J]. J Anim Sci, 2014, 92(2):549-560). In addition, Chinese Patent Application No. CN111676295A discloses a research method for genes related to feed intake regulation, and specifically discloses the design of primers for polymorphism detection based on the known duck CCK, CCKAR, NPY and NPY5R genes in NCBI GenBank, for use in SNP loci developed based on the above genes and related to duck feed intake. The results have shown that CCKAR gene has SNP loci related to duck feed intake, but SNP loci of CCK, NPY and NPY5R genes have not been reported yet. At present, there is no other literature about the fact that NPY and SNP loci related to duck feed intake have been developed.

In order to accurately select genotypes more suitable for growth and development and provide data for early breeding, the present disclosure provides a molecular marker for identifying traits of efficiency of duck feed utilization based on a neuropeptide gene NPY, a method and use thereof based on the above content.

SUMMARY

An objective of the present disclosure is to overcome the deficiencies in the prior art, and to provide a molecular marker for identifying traits of efficiency of duck feed utilization based on a neuropeptide gene NPY, a method and use thereof. Aiming to single nucleotide polymorphism (SNP) molecular markers of candidate genes related to the traits of efficiency of duck feed utilization, the present disclosure solves the problem of slow progress in conventional phenotypic breeding and realizes early identification of the traits of efficiency of feed utilization.

The present disclosure realizes the above objective through the following technical solutions:

The present disclosure provides a molecular marker for identifying traits of efficiency of duck feed utilization based on a neuropeptide gene NPY. The NPY gene has a nucleotide sequence shown in SEQ ID NO: 1, the molecular marker is T or C, and the molecular marker is located at position 577 of the nucleotide sequence.

The present disclosure further provides use of a molecular marker for identifying traits of efficiency of duck feed utilization based on a neuropeptide gene NPY in the identification of the traits of efficiency of duck feed utilization.

The present disclosure further provides a method for identifying traits of efficiency of duck feed utilization using the foregoing molecular marker, including the following steps:
- step 1, extracting total DNA from the venous blood of duck wings;
- step 2, designing primers for specific amplification using a sequence composed of a site where the molecular marker is located and upstream and downstream bases thereof as a target sequence; with the total DNA as a template, conducting PCR amplification to obtain a PCR product using the primers for specific amplification;
- step 3, genotyping and sequencing the PCR product to obtain a molecular marker type of a duck to be tested; and
- step 4, determining the traits of efficiency of duck feed utilization based on the molecular marker type.

A further improvement is that sequences of the primers for specific amplification are as follows:

```
SEQ ID NO: 2: Forward primer:
GGACATGGCCAGATACTACTCGG;
and

SEQ ID NO: 3: Reverse primer:
GGGTACATGACCCCTGCATCTTT.
```

A further improvement is that the genotyping is implemented by conducting native polyacrylamide gel electrophoresis and silver staining on the PCR product to acquire an image and genotyping based on the image, where the PCR product is:
(1) CC genotype on conditions that there are three bands;
(2) CT genotype on conditions that there are six bands; and
(3) TT genotype on conditions that there are five bands.

A further improvement is that specific steps of determining the traits of efficiency of duck feed utilization based on the molecular marker type in step 4 are as follows:
(1) the traits of efficiency of duck feed utilization being extremely high on conditions that the molecular marker type of the duck to be tested is CC genotype; and
(2) the traits of efficiency of duck feed utilization being fair on conditions that the molecular marker types of the duck to be tested are CT and TT genotypes.

The present disclosure has the following beneficial effects: The present disclosure provides a molecular marker for identifying traits of efficiency of duck feed utilization based on a neuropeptide gene NPY, a method and use thereof. Mutation of the NPY gene is detected using a polymerase chain reaction-single strand conformation polymorphism (PCR-SSCP) method, the traits of efficiency of duck feed utilization are selected based on genotypes, and a breeding method for early selection of efficiency of poultry feed utilization is established. The method is simple, rapid, and low-cost, does not need special instrument, and satisfies experimental needs.

DETAILED DESCRIPTION OF THE PREFERRED EMBODIMENTS

The present application will be described in further detail below with reference to the accompanying drawings. It should be pointed out herein that the following specific implementations are only intended to further explain the present application, rather than to be construed as limiting the protection scope of the present application. Those skilled in the art may make non-essential improvements and adjustments to the present application based on the above content.

1. Materials

All methods used in the examples are conventional methods known to those skilled in the art, unless otherwise specified; all materials and reagents used are commercially available, unless otherwise specified.

2. Method 2.1 Obtaining Polymorphic Loci of Duck NPY Gene 2.1.1 Genomic DNA Extraction and Detection Three hundred and eighty-eight male ducklings of white feather ducks (Q1 line) were selected, the blood was collected from the wing vein at the age of 42 days, and total DNA was extracted from the venous blood samples of duck wings using the Blood Genome DNA Extraction Kit produced by Takara Biotechnology (Dalian) Co., Ltd. Specific operations followed the instructions of the kit.

Figure 1:
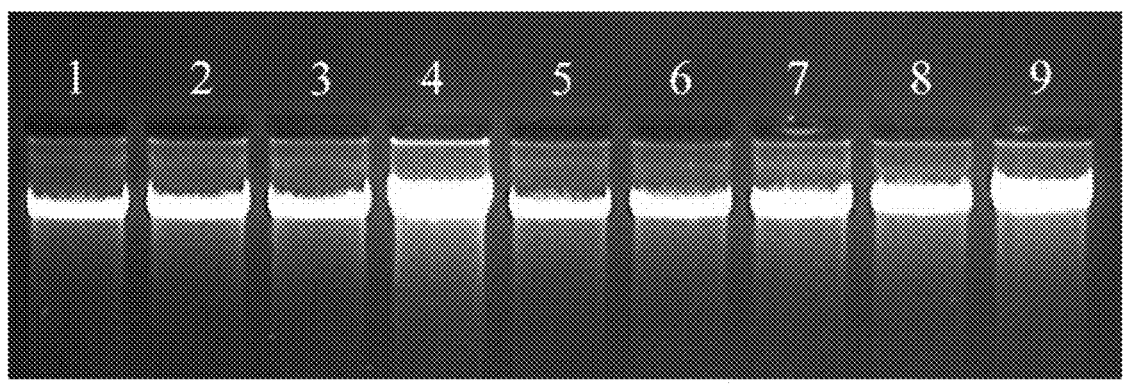
FIG. 1 illustrates the DNA electrophoresis result of extracted duck genome obtained by the kit method.

DNA concentration and OD value were measured with NanoDrop2000. DNA was detected by 1.5% agarose gel electrophoresis. The results are shown in FIG. 1. The quality of the extracted genomic DNA was good, and the main band was single and clear.

2.1.2 Primer Design

The DNA sequence corresponding to the NPY gene shown in SEQ ID NO: 1 (NCBI accession number is NC_051773) was found from the duck genome database. The partial DNA sequence of the NPY gene shown in SEQ ID NO: 1 was used as a template. During the primer design, attention should be paid to arrange the SNP locus in the middle position as much as possible, so as to avoid the occurrence of hairpin structures, primer dimers and mismatches and optimize the primer sequences. The primer sequences are shown as follows:

```
SEQ ID NO: 2: Forward primer:
GGACATGGCCAGATACTACTCGG;
and

SEQ ID NO: 3: Reverse primer:
GGGTACATGACCCCTGCATCTTT.
```

The length of the amplified fragment of the primer was 197 bp, and the sequence is shown in SEQ ID NO: 4, containing the molecular marker locus of T/C mutation at position 557.

2.1.3 PCR Amplification

Using Mix produced by Sangon Biotech (Shanghai) Co., Ltd., the target fragment of the NPY gene was subjected to PCR amplification through the synthesized sequencing-specific primers. The PCR amplification system was as follows:

| Component | Volume |
| --- | --- |
| DNA template | 0.8 μL |
| Forward primer | 0.1 μL |
| Reveres primer | 0.1 μL |
| Mix | 7 μL |
| ddH$_2$O | 7 μL |
| Total | 20 μL |

The PCR program was as follows: initial denaturation at 95° C. for 5 min; step 1, denaturation at 95° C. for 45 s; step 2, annealing at 62° C. for 45 s (annealing temperature depended on the primers); step 3, extension at 72° C. for 30 s, where steps 2 and 3 were cycled 31 times, with a total of 32 cycles; and extension at 72° C. for 10 min.

2.1.4 Detection of PCR Products

Figure 2:
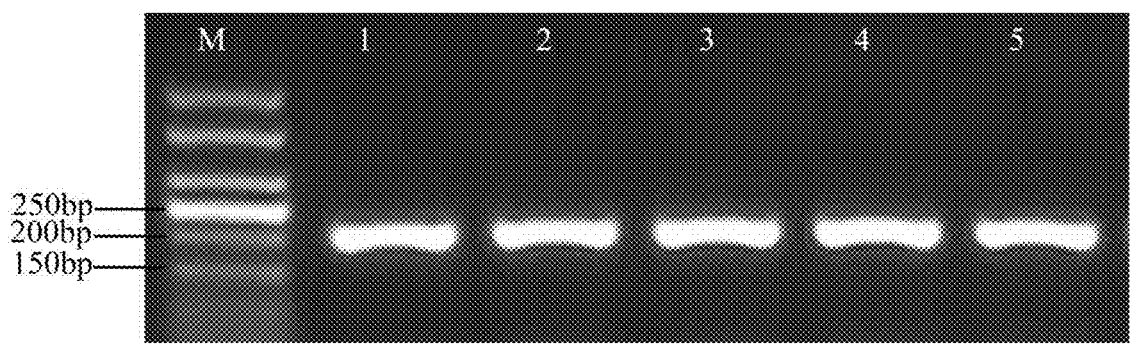
FIG. 2 is an electrophoretogram of specifically amplified products of some samples, where M represents 1 kb DNA Marker, and lanes 1 to 5 represent bands of specifically amplified products.

The PCR product was detected by 1 wt % agarose gel electrophoresis, as shown in FIG. 2, and a band with a length of approximately 200 bp was obtained after imaging on a gel imager, which was consistent with the predicted length, indicating that the target fragment was obtained. The PCR product was submitted to Sangon Biotech (Shanghai) Co., Ltd. for sequencing. The sequence is shown in SEQ ID NO: 4, which is consistent with the predicted result.

2.1.5 Denaturation of PCR Product and SSCP Detection

The PCR product was first denatured and then subjected to polyacrylamide gel electrophoresis (PAGE), and finally its mutation was determined according to the results of different banding patterns. The specific steps were as follows:

(1) A native polyacrylamide gel was prepared according to the instructions. The native acrylamide gel system is as follows:

| Concentration | Acr/Bis solution | | Consumption (mL) | 5 × TBE (mL) | ddH$_2$O (mL) | APS (μL) | TEMED (μL) |
| --- | --- | --- | --- | --- | --- | --- | --- |
| | Degree of crosslinking | Concentration (%) | | | | | |
| 12 | 29:1 | 30 | 14 | 7 | 14 | 476.5 | 50 |

(2) TEMED was finally added, and poured into the mold immediately after adding (make sure that the mold is closed before pouring to prevent gel leak when pouring, and that the size of the gel strip is consistent with that of the comb); the mold was tilted at an angle of about 45°, and the gel liquid was poured slowly from the center of the vertical slab (which can effectively avoid the generation of bubbles); the pouring was stopped when it was about away from the upper edge of the mold; a comb prepared in advance was inserted, the gel was polymerized at room temperature for 40 min, and the excess acrylamide was stored at 4° C.; the gel polymerization on the glass plate was observed at any time, and an appropriate amount of native acrylamide gel system mixture was replenished.

(3) A slab was prepared during the gel polymerization waiting process. After the polymerization was completed, a glass plate was mounted, 1×TBE was added to the slab so that the TBE solution exceeded the sample wells by about 3 cm, and the air bubbles were removed therefrom.

(4) 3 μL of PCR product was pipetted into a PCR tube, supplemented with 7 μL of denaturing reagent, briefly centrifuged to mix well, and denatured at 98° C. for 10 min; the PCR tube was quickly taken out and put in a −20° C. ice box for 10 min, and the sample was loaded with a 10 μL pipette.

(5) The power was turned on, the electrophoresis was run at 220 V for 10 min, the voltage was modulated to 120 V, and the electrophoresis was run for 21 h.

(6) After electrophoresis, the electrophoresis apparatus was turned off, the glass plate was taken out, and the gel was carefully removed and put in a white porcelain dish filled with clean water to wash once or twice.

(7) The gel was placed in the dye solution and shaken gently in the dark for 15 min. The dye solution was composed of silver nitrate and pure water, and the concentration of silver nitrate was 0.2%.

(8) After dyeing, AgNO$_3$ was recovered, the gel was washed 1-3 times with deionized water, for 2 min each time, and the excess dye solution was washed away.

(9) Bands were developed with colorimetric solution to make them clear and the background light yellow. The dyeing could not stop until the bands were clearly visible, and the colorimetric solution was discarded immediately after the color development. The colorimetric solution was 500 mL in volume, containing 2% NaOH+0.04% Na$_2$CO$_3$+420 μL formaldehyde.

(10) A picture was taken and saved.

2.1.6 Genotyping

Figure 3:
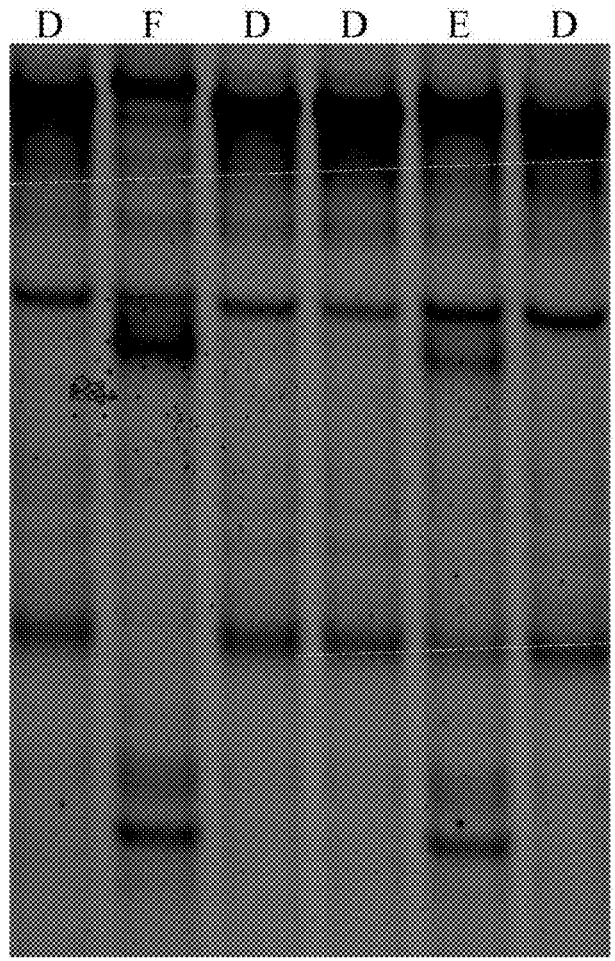
FIG. 3 is an electrophoretogram showing genotyping of specifically amplified products of some samples.

The PCR-SSCP pattern is shown in FIG. 3. Different banding patterns indicate different genotypes. It can be seen from FIG. 3 that there are three genotypes at position 577 of the NPY gene, namely TT, CT, and CC.

(1) The result was CC genotype when there were three bands;

(2) the result was CT genotype when there were six bands; and (3) the result was TT genotype when there were five bands.

2.1.7 DNA Verification and Sequencing

Figure 4:
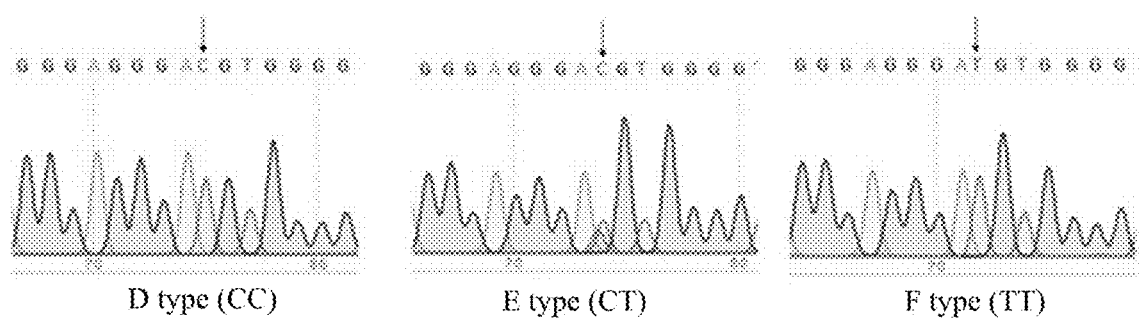
FIG. 4 illustrates the verification and sequencing results of genotypes at position 557 in NPY gene, showing fragments in D type (SEQ ID NO: 5), E type (SEQ ID NO: 6), and F type (SEQ ID NO: 7).

Colorimetric genotyping gel maps were counted to obtain three genotypes, TT, CT, and CC. One individual was selected for sequence alignment of these three genotypes, respectively. The sequence alignment is shown in FIG. 4; in the sequencing results, T is mutated to C, and the arrow marks the mutation site, which is consistent with the PCR-SSCP result.

2.2 Association Analysis Between the T577C Mutation Site of NPY Gene and the Traits of Efficiency of Duck Feed Utilization

2.2.1 Genotyping

To determine whether the T/C polymorphism at base 557 (T557C) of NPY exon 1 in white feather ducks (Q1 line) was associated with the traits of efficiency of meat duck feed utilization, 388 drakes of white feather duck (Q1 line) were used as experimental material, and statistics were made on the body weight at 21 days (BW21), body weight at 42 days (BW42), residual feed intake (RFI), average daily feed intake (ADFI), average daily gain (ADG), feed conversation ratio (FCR), and metabolic body weight (MBW) of meat ducks aged 21-42 weeks. Individual RFI, ADFI, MBW, and BWG were calculated according to the following formulas:

$$RFI=FI-(b_0+b_1*MBW^{0.75}+b_2*BWG)$$

$$ADFI=(FI42-FI21)/21 \text{ (average feed intake of 21-42 days)}$$

$$MBW^{0.75}=[(BW21+BW42)/2]0.75$$

$$ADG=(BW42-BW21)/21$$

where RFI is the residual feed intake; FI is the daily feed intake of an individual; $MBW^{0.75}$ is the average metabolic body weight; ADG is the average daily gain; $b_0$ is the intercept, and $b_1$ and $b_2$ are regression coefficients. The calculation of RFI was done by the SAS linear fitting function. Three hundred and eighty-eight ducks were genotyped by the genotyping method in Section 2.1.6. The results are shown in Table 1.

TABLE 1

Genotyping results of individuals with different phenotypes

| | Genotype | | |
|---|---|---|---|
| | TT | CT | CC |
| Number | 197 | 170 | 21 |
| $\chi^2$-test | | $\chi^2 = 4.1407, P = 0.1261$ | |

The chi-square test showed that the genotypes of the experimental duck flock were in Hardy-Weinberg equilibrium.

2.2.2 Statistical Analysis

The numbers of TT, CT and CC genotypes were counted from the gel map, and the differences between the three genotypes and slaughter performance were analyzed by one-way ANOVA in SPSS20.0. The results of association analysis between different genotypes and various traits are shown in Table 2:

TABLE 2

Analysis association between duck NPY genotypes and traits of efficiency of duck feed utilization

| | | Genotype | | |
|---|---|---|---|---|
| | | CC | CT | TT |
| Growth and feed efficiency traits | BW42 (g) | 3842.49 ± 273.79 | 3860.21 ± 291.85 | 3764.50 ± 292.97 |
| | FI (g) | 266.27 ± 22.77$^a$ | 272.25 ± 27.09$^b$ | 266.29 ± 23.93$^a$ |
| | BWG (g) | 132.07 ± 11.97 | 132.83 ± 12.97 | 130.21 ± 12.82 |
| | $MBW^{0.75}$ | 348.71 ± 17.07 | 349.73 ± 18.14 | 342.45 ± 18.60 |
| | FCR | 2.02 ± 0.11 | 2.06 ± 0.16 | 2.05 ± 0.12 |
| | RFI | −3.23 ± 12.60$^a$ | 1.52 ± 16.99$^b$ | 1.99 ± 13.00$^b$ |

NOTE:
Different lowercase letters in the same row indicate significant difference (P < 0.05), and no letter indicates no significant difference (P > 0.05).

According to the table, it was concluded through the comparison of feed efficiency traits of individuals with different genotypes that, among drakes CC, CT and TT genotypes, drakes with CC genotype had significantly lower FI and RFI, especially RFI, than those with CT and TT genotypes (P<0.05), and there was no significant difference in other indicators among the genotypes (P>0.05). Since RFI is a negative selective trait, it was concluded that individuals with CC genotype had extremely high feed conversion traits, while those with CT and TT genotypes had fair feed conversion traits.

The above examples merely represent several embodiments of the present disclosure, and the descriptions thereof are specific and detailed, but they should not be construed as limiting the patent scope of the present disclosure. It should be noted that those of ordinary skill in the art can further make several variations and improvements without departing from the concept of the present disclosure, and all of these fall within the protection scope of the present disclosure.

What is claimed is:

1. A method for identifying feed intake (FI), relative feed intake (RFI) and feed conversion of a duck, the method comprising:
   a). extracting total DNA from the venous blood of duck wings;
   b). conducting PCR amplification on the total extracted DNA using forward primer, SEQ ID NO: 2 and reverse primer, SEQ ID NO: 3;
   c). subjecting the PCR product to polymerase chain reaction single strand conformation polymorphism (PCR-SSCP) and sequencing neuropeptide gene, NPY, comprising the nucleotide of SEQ ID NO 1 to determine both alleles at position 557 of SEQ ID NO 1 to obtain a genotype of the duck; and
   d). determining the FI, RF1, and feed conversion based on the genotype of the duck determined in step c) wherein a CC genotype indicates a lower FI, lower RFI, and extremely high feed conversion than ducks with a CT and TT genotypes.

* * * * *